United States Patent
Chiel et al.

(10) Patent No.: US 10,758,738 B2
(45) Date of Patent: Sep. 1, 2020

(54) SYSTEMS AND METHODS FOR FAST AND REVERSIBLE NERVE BLOCK

(71) Applicant: CASE WESTERN RESERVE UNIVERSITY, Cleveland, OH (US)

(72) Inventors: Hillel Chiel, Cleveland, OH (US); Niloy Bhadra, Cleveland, OH (US); Mike Jenkins, Cleveland, OH (US); Emilie Lothet, Cleveland, OH (US); Tina Vrabec, Cleveland, OH (US); Kevin Kilgore, Cleveland, OH (US); Narendra Bhadra, Cleveland, OH (US); Eric Duco Jansen, Cleveland, OH (US)

(73) Assignees: CASE WESTERN RESERVE UNIVERSITY, Cleveland, OH (US); VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/126,610

(22) PCT Filed: Mar. 17, 2015

(86) PCT No.: PCT/US2015/020951
§ 371 (c)(1),
(2) Date: Sep. 16, 2016

(87) PCT Pub. No.: WO2015/142838
PCT Pub. Date: Sep. 24, 2015

(65) Prior Publication Data
US 2017/0080244 A1 Mar. 23, 2017

Related U.S. Application Data

(60) Provisional application No. 61/954,915, filed on Mar. 18, 2014.

(51) Int. Cl.
*A61N 1/40* (2006.01)
*A61N 5/06* (2006.01)
(Continued)

(52) U.S. Cl.
CPC .............. *A61N 1/403* (2013.01); *A61F 7/007* (2013.01); *A61N 1/06* (2013.01); *A61N 1/28* (2013.01);
(Continued)

(58) Field of Classification Search
CPC .. A61N 1/403; A61N 5/0622; A61N 1/36071; A61N 7/02; A61N 5/0625;
(Continued)

(56) References Cited

U.S. PATENT DOCUMENTS

2009/0149926 A1* 6/2009 Dacey, Jr. .............. A61B 5/411
607/96
2011/0092880 A1* 4/2011 Gertner .................. A61B 5/412
604/20

FOREIGN PATENT DOCUMENTS

WO 2009058258 A1 5/2009
WO 2009073208 A1 6/2009
(Continued)

OTHER PUBLICATIONS

Russo, Marc, and Jean-Pierre Van Buyten. "10-kHz high-frequency SCS therapy: a clinical summary." Pain Medicine 16.5 (2015): 934-942.
(Continued)

*Primary Examiner* — Bo Joseph Peng
(74) *Attorney, Agent, or Firm* — Tarolli, Sundheim, Covell & Tummino LLP (57) ABSTRACT

One aspect of the present disclosure relates a system that can quickly and reversibly block conduction in a nerve. The system can include a first nerve block modality that provides
(Continued)

heat to the nerve to block conduction in the nerve. For example, the heat can provide the quick nerve block. The system can also include a second nerve block modality that provides an electrical signal to the nerve to block the conduction in the nerve. For example, the electrical signal can provide the reversibility. In some instances, the heat can be provided by an infrared light signal and the electrical signal can be provided by a kilohertz frequency alternating current (KHFAC) signal or a direct current (DC) signal.

3 Claims, 10 Drawing Sheets

(51) Int. Cl.
  *A61N 7/02*    (2006.01)
  *A61N 1/06*    (2006.01)
  *A61N 1/28*    (2006.01)
  *A61N 1/36*    (2006.01)
  *A61F 7/00*    (2006.01)
  *A61N 5/067*    (2006.01)
  *A61N 7/00*    (2006.01)

(52) U.S. Cl.
  CPC ..... *A61N 1/36067* (2013.01); *A61N 1/36071* (2013.01); *A61N 5/0622* (2013.01); *A61N 5/0625* (2013.01); *A61N 7/02* (2013.01); *A61F 2007/0071* (2013.01); *A61N 2005/067* (2013.01); *A61N 2005/0659* (2013.01); *A61N 2007/0021* (2013.01)

(58) Field of Classification Search
  CPC ........ A61N 1/06; A61N 1/36067; A61N 1/28; A61N 2005/067; A61N 2007/0021; A61N 2005/0659; A61F 7/007; A61F 2007/0071
  See application file for complete search history.

(56) References Cited

FOREIGN PATENT DOCUMENTS

WO    2009075783 A1   6/2009
WO    2013188753 A1   12/2013

OTHER PUBLICATIONS

Stetkarova, Ivana, et al. "Intrathecal baclofen in spinal spasticity: frequency and severity of withdrawal syndrome." Pain physician 18.4 (2015): E633-E641.
International Search Report for corresponding PCT/US2015/020951 dated Jul. 7, 2015, pp. 1-13.
Abaya TV, Diwekar M, Blair S, Tathireddy P, Rieth L, Clark GA, Solzbacher F. Characterization of a 3D optrode array for infrared neural stimulation, Biomed Opt Express. Sep. 1, 2012;3(9):2200-19. Epub Aug. 24, 2012.
Abel NA, Smith RA. (1994) Intrathecal baclofen for the treatment of intractable spasticity. Arch Phys Med Rehabil. 75:54-58.
Ackermann D, Foldes EL, Bhadra N, Kilgore KL, Electrode design for high frequency block: effect of bipolar separation on block thresholds and the onset response. Conf Proc IEEE Eng Med Biol Soc. 654-7, 2009a.
Ackermann DM, Jr., Foldes EL, Bhadra N, Kilgore KL, Effect of bipolar cuff electrode design on block thresholds in high-frequency electrical neural conduction block. IEEE Trans Neural Syst Rehabil Eng, 17 (5):469-77, 2009b.
Ackermann D, Reduction of the Onset Response in High Frequency Nerve Block, Cleveland, OH, USA: Case Western Reserve University; 2010.
Ackermann DM, Jr., Foldes EL, Bhadra N et al. Conduction block of peripheral nerve using high-frequency alternating currents delivered through an intrafascicular electrode. Muscle Nerve 2010a; 41 (1):117-9.
Ackermann DM, Bhadra N, Foldes EL, Wang X, Kilgore KL, Effect of nerve cuff electrode geometry on onset response firing in conduction block of whole nerve using high frequency alternating currents, IEEE Trans Neural Syst Rehabil Eng, 18(6):658-65, 2010b.
Ackermann DM, Foldes EL, Bhadra N, Kilgore KL, Nerve conduction block using combined thermoelectric cooling and high frequency electrical stimulation, J Neuroscience Methods, 193(1):72-6, 2010c.
Ackermann, DM, Bhadra N, Foldes EL, Kilgore KL, Conduction block of whole nerve without onset firing using combined high frequency and direct current, Med & Biol Eng & Comput, 49(2):241-51, 2011a.
Ackermann DM, Bhadra N, Foldes EL, Kilgore KL, Separated Interface Nerve Electrode Prevents Direct Current Induced Nerve Damage, J. Neuroscience Methods, Sep. 30; 201(1):173-6, 2011b.
Ackermann DM, Ethier C, Foldes EL, Oby ER, Tyler D, Bauman M, Bhadra N, Miller L, Kilgore KL, Electrical conduction block in large nerves: high frequency current delivery in the nonhuman primate, Muscle & Nerve, 43(6):897-9, 2011c.
Ackermann, DM, Bhadra N, Gerges M, Thomas PJ. Dynamics and sensitivity analysis of high-frequency conduction block. J Neural Eng. 8(6):065007, 2011d.
Adamczyk MM, Crago PE, Input-output nonlinearities and time delays increase tracking errors in hand grasp neuroprostheses IEEE Trans Rehabil Eng. Dec. 1996:4(4):271-9. Review.
Adams MM, Hicks AI, Spasticity after spinal cord injury, Spinal Cord, 43, 577-586, 2005.
Andreani, Juan Carlos M., and Cristina Guma. "New Animal Model to Mimic Spastic Cerebral Palsy: The Brain-Damaged Pig Preparation." Neuromodulation: Technology at the Neural Interface 11, No. 3 (2008): 196-201.
Al-Khodairy AT, Gobelet C, Rossier AB. (1998) Has botulinum toxin type A a place in the treatment of spasticity in spinal cord injury patients? Spinal Cord. 36:854-858.
Azizi, F., Lu, H., Chiel, H. J., and Mastrangelo, C. H. (2010) Chemical neurostimulation using pulse code modulation (PCM) microfluidic chips. Journal of Neuroscience Methods, 192:193-8.
Bhadra N, Peckham PH, Michael W. Keith MW, Kevin L. Kilgore KL, Montague F, Gazdik M, and Stage T. "Implementation of an implantable joint-angle transducer." Journal of rehabilitation research and development 39, No. 3, (2002), 411-422, 2002.
Bhadra N. Bhadra N, Kilgore KL, Gustafson KJ, High frequency electrical conduction block of the pudendal nerve, J Neural Eng, 3 (2): 180-7, 2006.
Bhadra N, Kilgore KL, Direct current electrical conduction block of peripheral nerve, IEEE Trans Neural Syst Rehabil Eng 2004a; 12 (3):313-24.
Bhadra N, Kilgore KL, High-frequency electrical conduction block of mammalian peripheral motor nerve. Muscle Nerve 2005; 32 (6):782-90.
Bhadra N, Foldes EL, Ackermann D, Kilgore KL, Reduction of the onset response in high frequency nerve block with amplitude ramps from non-zero amplitudes. Conf Proc IEEE Eng Med Biol Soc; 650-3: 2009.
Bhadra N, Lahowetz EA, Foldes ST et al. Stimulation of high-frequency sinusoidal electrical block of mammalian myelinated axons. J Comput Neurosci. 22(3):313-26, 2007.
Bhadra N, Peckham PH, Keith MW, Kilgore KL, Montague FW, Gazdik MM and Stage T: Implementation of an Implantable Joint Angle Transducer, J Rehabil Res Dev, 39 (3):411-422, 2002.
Bhadra N, Grünewald V, Creasey G, and Mortimer JT. "Urethral pressure profiles in the female canine implanted with sacral anterior nerve root electrodes," World journal of urology 19, No. 4 (2001): 272-277.
Boger A, Bhadra N, Gustafson KJ. Bladder voiding by combined high frequency electrical pudendal nerve block and sacral root stimulation, Neurourology and Urodynamics 2008; 27 (5):435.
Boger AS, Bhadra N, Gustafson KJ. High frequency sacral root nerve block allows bladder voiding. Neurourol Urodyn;31(5):677-82, 2012.

(56) References Cited

OTHER PUBLICATIONS

Bowman B, McNeal D. Response of Single Alpha Motorneurons to High-Frequency Pulse Trains, Appl. Neurophysiol. 1986; 49:121-38.

Cayce J, Friedman R, Jansen ED, Mahadevan-Jansen A, Roe A—Pulsed infrared light alters neural activity in rat somatosensory cortex in vivo—NeuroImage 57, 155-166 (2011).

Cayce JM, Friedman RM, Chen G, Jansen ED, Mahadevan-Jansen A, Roe AW—Infrared neural stimulation of primary visual cortex in non-human primates—NeuroImage, 84: 181-190 (2013).

Cayce JM, Kao CC, Malphrus JD, Konrad PE, Mahadevan-Jansen A, Jansen ED—Infrared Neural Stimulation of Thalamocortical Brain Slices—IEEE J Spec Topics Quantum Electr 16(3): 565-72 (2010).

Coffey RJ, Edgar TS, Francisco GE, Graziani V, Meythaler JM, Ridgely PM, Sadiq SA, Turner MS, Abrupt withdrawal from intrathecal Baclofen: recognition and management of a potentially life-threatening syndrome, Arch Phys Med & Rehabil, 83(6):735-741, 2002.

Cohen, Mark L, and Zhanna Georgievskaya, "Histopathology of the stimulated vagus nerve: primum non nocere," Heart failure reviews 16, No. 2, 163-169, 2011.

Cullins, M. J. and Chiel, H.J. (2010). Electrode fabrication and implantation in Aplysia californica for multi-channel neural and muscular recordings in intact, freely behaving animals. Journal of Visualized Experiments, doi:10.3791/1791. PMCID: PMC3153892.

Damiano DL, Alter KE, Chambers H, New clinical and research trends in lower extremity management for ambulatory children with cerebral palsy, Phys Med Rehabil Clin N Am. 20(3):469-491, 2009.

Dimarco AF, Kowalski KE. Activation of inspiratory muscles via spinal cord stimulation. Respir Physiol Neurobiol. S1569-9048(13)00198-5. doi: 10.1016/j.resp.2013.06.001. [Epub ahead of print]. 2013.

Dittami GM, S. M. Rajguru, R. A Lasher, R. W. Hitchcock, and R. D. Rabbitt, "Intracellular calcium transients evoked by pulsed infrared radiation in neonatal cardiomyocytes," The Journal of Physiology 589, 1295-1306 (2011).

Duke, A. R., Lu, H., Jenkins, M. W., Chiel, H J. and Jansen, E. D. (2012) Spatial and temporal variability in response to hybrid electro-optical stimulation. Journal of Neural Engineering 9: 036003. doi.10.1088/1741-2560/9/3/035003.

Duke, A. R., Jenkins, M. W., Lu, H., McManus, J. M., Chiel, H. J. and Jansen, E. D. Reversible and selective inhibition of neural activity with infrared light. Scientific Reports, (a Nature journal) 3:2600, doi: 10.1038/srep02600.

Duke AR, Cayce JM, Malphrus JD, Konrad PE, Mahadevan-Jansen A, Jansen ED—Combined optical and electrical stimulation of neural tissue in vivo—J Biomed Optics 14. 060501 (2009).

Duke AR, Peterson E, Mackanos MA, Atkinson J, Tyler D, Jansen ED—Hybrid electro-optical stimulation of the rat sciatic nerve induces force generation in the plantarflexor muscles—Journal of Neural Engineering 9(6) (2012) DOI: 10.1068/1741-2560/9/6/066005.

Duke AR, Jenkins M, Lu H. McManus JM, Chiel HJ, Jansen ED—Transient and selective suppression of neural activity with infrared light—Scientic Reports 3:2600 (2013). DOI: 10.1038/srep02600.

Durfee WK, Mariano TR, Zahradnik JL, Simulator for evaluating shoulder motion as a command source for FES grasp restoration system, Arch Phys Med Rehabil. Dec. 1991;72(13). 1088-94.

Feng HJ, Kao CC, Gallagher MJ, Jansen ED, Mahadevan-Jansen A, Konrad PE, MacDonald RL—Alteration of GABAergic neurotransmission by pulsed infrared laser stimulation—J Neurosci Meth, 192(1), 110-114 (2010).

Flett PJ. Rehabilitation of spasticity and related problems in childhood cerebral palsy. J Paediatr Child Health. 39(1):6-14; 2003.

Foldes EL, Ackermann D, Bhadra N et al. Counted cycles method to quantify the onset response in high-frequency peripheral nerve block, Conf Proc IEEE Eng Med Biol Soc. 614-7. 2009.

Foldes EL, Ackermann EM, Bhadra N, Kilgore KL, Bhadra N, Design, fabrication and evaluation of a conforming circumpolar peripheral nerve cuff electrode for acute experimental use. J Neurosci Methods. 196(1):31-37, 2011.

Franke M. Bhadra N, Bhadra N, Kilgore KL, Gustafson KJ. Chronic bladder control post SCI via Electric Pudendal Nerve Block. Accepted for NER Conference, Engineering in Medicine and Biology, 2013.

Fried NM, G. A. Lagoda, N. J. Scott, L. M. Su, and A. L. Burnett, "Noncontact stimulation of the cavernous nerves in the rat prostate using a tunable-wavelength thulium fiber laser," J Endourol 22, 409-413 (2008).

Fu X. Z. Wang, Y. T. Wang, M. W. Jenkins, and A. M. Rollins, "Catheter Polarization-sensitive OCT for Cardiac Radiofreuency Ablation," in SPIE BIOS, (San Francisco, 2013).

Gaunt R, Prochazka A. Transcutaneously coupled, high-frequency electrical stimulatation of the pudendal nerve blocks external urethral sphincter contractions. Neurorehabil Neural Repair 2009, 23:615.

Gerges M, Foldes EL, Ackermann DM, Bhadra N, Bhadra N, Kilgore KL, Frequency and amplitude transitioned waveforms mitigate the onset response in high frequency nerve block, J Neural Eng, 7(6):066003, 2010.

Goyal V. S. Rajguru, A. I. Matic, S. R. Stock, and C. P. Richter, "Acute damage threshold for infrared neural stimulation of the cochiea: functional and histological evaluation," Anat Rec (Hoboken) 295, 1987-1999 (2012).

Gracies JM, Elovic E, McGuire J, Simpson D, Traditional pharmacological treatments for spasticity part I: Local treatments, Muscle Nerve Suppl. 20(Supplement 6):61-91, 1997a.

Gracies JM, Nance P, Elovic E, McGuire J, Simpson DM, Traditional pharmacolgical treatments for spasticity, Part II: General and regional treatments, Muscle Nerve Suppl. 6:S92-120, 1997b.

Grill WM, Mortimer JT, Neural and connective tissue response to long-term implantation of multiple contact nerve cuff electrodes. J Biomed Mater Res, 50 (2)215-26, 2000.

Halpern, J. M., Xie, S., Sutton, G. P., Higashikubo, B. T., Chestek, C. A., Lu, H., Chiel, H. J. and Martin, H. B. (2006) Diamond electrodes for neurodynamic studies in Aplysia californica, Diamond and Related Materials, 15:183-187.

Hansen CR, Gooch JL. Such-Neibar T (2007) Prolonged, severe intrathecal baclofen withdrawal syndrome: a case report. Arch Phys Med Rehabil. 88(11) 1468-71.

Hines AE, Crago PE, Billian C. Functional electrical stimulation for the reduction of spasticity in the hemiplegic hand Biomed Sci Instrum. 1993:29:259-66.

Hodgkin AL and B. Katz, "The effect of temperature on the electrical activity of the giant axon of the squid," J Physiol 109, 240-249(1949).

Huxley AF, "Ion movements during nerve activity," Ann N Y Acad Sci 81, 221-246 (1959).

Izzo AD, J. T. Walsh, Jr., H. Ralph, J. Webb, M. Bendett, J. Wells and C. P. Richter, "Laser stimulation of auditory neurons effect of shorter pulse duration and penetration depth," Biophys J 94, 3159-3166 (2008).

Izzo AD, Richter CP, Jansen ED, Walsh JT—Laser Stimulation of the Auditory Nerve—Lasers Surg Med 36(7): 745-53 (2006).

Izzo AD, Jansen ED, Richter CP, Walsh JT—Optical Parameter Variability in Laser Nerve Stimulation: a study of pulse duration, repetition rate, and wavelength—IEEE Transactions on Biomed Eng 54(6): (2007).

Jenkins MW, Duke AR, Gu S, Chiel HJ, Watanabe M, Jansen ED, Rollins AM—Optical pacing of the embryonic heart—Nature Photonics, Aug. 15. doi:10.1038/nphoton.2010.166 (2010).

Johnson MW, Peckham PH, Bhadra N, Kilgore KL, Gazdik MM, Keith MW, Strojnik P: An Implantable Transducer for Two-Degree-of-Freedom Joint Angle Sensing IEEE Trans. Biomed. Eng., 7(3):349-359, 1999.

Johnston, Michael V., Donna M. Ferriero, Susan J. Vannucci, and Henrik Hagberg, "Models of Cerebral Palsy Which Ones are Best?," Journal of child neurology 20, No. 12 (2005): 984-987.

(56) References Cited

OTHER PUBLICATIONS

Joseph L., Bureta RJ. Unmyelinated Aplysia nerves exhinit a non monotonic blocking response to high frequency stimulation. IEEE Transactions on Neural Systems and Rehabilition Engineering 2009; 17 (6):537-44.

Kang W, H, Wang, Z. Wang, M. W. Jenkins, G. A. Isenberg, A. Chak and A. M. Rollins, "Motion artifacts associated with in vivo endoscopic OCT images of the esophagus," Opt. Express, 19(21) pp. 20722-20735 (2011), PMID.

Kang W. H. Wang, Y. Pan, M. W. Jenkins, G. A. Isenberg, A. Chak, M. Atkinson, D. Agrawal, Z. Hu and A. M. Rollins, "Endoscopically guided spectral-domain OCT with double-ballon catheters," Opt. Express, 18(16) pp. 17364-17372 (2010). PMID: 20721123.

Kilgore KL. Scherer M. Bobblitt R, Dettloff J, Dombrowski DM, Godbold N, Jatich JW, Morris R. Penko JS, Schremp ES, Cash LA, Neuroprosthesis consumers' forum: consumer priorities for research directions, J Rehabilitation Research and Development, 38:655-660, 2001.

Kilgore K, Foldes E, Ackermann D et al. Combined direct current and high frequency nerve block for elmination of the onset response. In Engineering in Medicine and Biology Society, 2009, 197-9 p.

Kilgore KL, Bhadra N. Nerve conduction block utilising high-frequency alternating current. Med Biol Eng Comput 2004: 42 (3):394-406.

Kilgore KL, Hoyen HA, Bryden AM, Hart RL, Keith MW, Peckham PH, Montague FW, Sams CJ, Bhadra N, An Implanted Upper Extremity Neuroprosthesis Utilizing Myoelectric Control, Journal of Hand Surgery, 33A:539-550, 2008. NIHMSID 125325.

Kilgore KL, Foldes EA, Ackermann DM et al. Combined direct current and high frequency nerve block for elimination of the onset response. Conf Proc IEEE Eng Med Biol Soc 2009b; 2009: 197-9.

Kilgore KL, Bhadra N. Reversible Nerve Conduction Block Using Kilohertz Frequency Alternating Current Review article. In Press. Neuromodulation, 2013.

Lewis KS, Mueller WM (1993) Intrathecal baclofen for severe spasticity secondary to spinal cord injury. Ann Pharmacother, 27(6):767-74.

Little JW, Massagli TL, Spasticity and Associated Abnormalities of Muscle Tone in Rehabilitation Medicine Principles and Practice, 3rd Edition, Eds. DeLisa JA and Gans BM, Lippincott-Raven Publishers, Philadelphia, PA, c.1998.

Lu, H., Chestek, C. A., Shaw, K. M., and Chief, H. J. (2008) Selective extracellular stimulation of individual neurons in ganglia. Journal of Neural Engineering. 5: 287-309.

Lu, H., McManus, J.M., Chiel, H. J. (2013) Extracellularly identifying motor neurons for a muscle motor pool in Aplysia californica. Journal of Visualized Experiments (73) e50189, doi. 10.3791/50189.

Matic AI, A. M. Robinson, H. K. Young, B. Badofsky, S. M. Rajguru, S. Stock, and C. P. Richter, "Behavioral and electrophysiological responses evoked by chronic infrared neural stimulation of the cochlea," PLoS One 8, e58189 (2013).

McCreery. Comparison of neural damage induced by electrical stimulation with faradaic and capacitor electrodes. Annals of Biomedical Engineering 1968: 16 (5) 463.

McCreery DB, Yuen TG, Agnew WF et al. A quantiative computer-assisted morphometric analysis of stimulation-induced injury to myelinated fibers in a peripheral nerve. J Neurosci Methods, 73 (2): 159-68, 1997.

McManus, J. M., Lu, H., Chief, H. J. (2012) An in vitro preparation for eliciting and recording feeding motor programs with physiological movements in Aplysia californica. Journal of Visualized Experiments (70), e4320, doi: 10.3791/4320.

Memberg WD, Murray WM, Ringleb SI, Kilgore KL, Snyder SA. A transducer to measure isometric elbow moments. Clin Biomech (Bristol, Avon). 16(10):918-20. 2001.

Mi Y, Sun C, Yao C et al. Effects of steep pulsed electric fields (SPEF) on mitochondrial transmembrane potential of human liver cancer cell. Conf Proc IEEE Eng Med Biol Soc 2007; 2007:5815-8.

Midha M, Schmitt JK (1998) Epidural spinal cord stimulation for the control of spasticity in spinal cord injury patients long-term efficacy and is not cost-effective. Spinal Cord, 36(3):190-2.

Miles JD, Kilgore KL, Bhadra N et al. Effects of ramped amplitude waveforms on the onset response of high-frequency mammalian nerve block. J Neural Eng, 4 (4):390-8, 2007.

Molenaers G, Van Campenhout A, Fagard K. De Cat J. Desloovere K, The use of botulinum toxin A in childrem with cerebral palsy, with a focus on the lower limb. J Child Orthop. 4(3):183-95, 2010.

Moore, L. E., J. P. Holt Jr, and B. D. Lindley (1972) "Laser temperature-jump technique for relaxation studies of the ionic conductances in myelinated nerve fibers." Biophysical journal 12.2: 157-174.

Moore, L. E. (1975) "Membrane conductance changes in single nodes of Ranvier, measured by laser-induced temperature-jump experiments." Biochimica et Biophysica Acta (BBA)—Biomembranes 375.1: 115-123.

Mou Z. I. F. Triantis, V. M. Woods, C. Toumazou, and K. Nikotic, "A simulation study of the combined thermoelectric extracellular stimulation of the sciatic nerve of the Xenopus laevis: the localized transient heat block."IEEE Trans Biomed Eng 59, 1758-1769 (2012).

Msaddi AK. Mazroue AR, Shahwan S, al Amri N, Dubayan N, Livingston D. Moutaery KR (1997) Stereotact Funct Neurosurg. 69(1-4 Pt 2):251-8.

Naples GG, Mortimer JT, Acheiner A, Sweeney JD. A spiral nerve cuff electrode for peripheral nerve stimulation. IEEE Trans Biomed Eng. Nov. 1988:35(11):905-16.

Novachek TF, Gage JR, Orthopaedic management of spasticity in cerebral palsy. Childs Nerv Syst 23(9):1015-31, 2007.

Oliveira JMA, Mitochondrial Membrane Potential and Dynamics. In: AK Reeve; KJ Krishnan, MR Duchen et al., editors, translator and editor Mitochondrial Membrane Potential and Dynamics. London: Springer-Verlag; 2012; p. 127-39.

Papavasiliou AS, Nikaina I, Bouros P, Rizou I, Filiopoulos C. Botulinum toxin treatment in upper limb spasticity treatment consistency. Eur J Paediatr Neurol. 16(3):237-42, 2012.

Polasek, Katharine H,. Harry A. Hoyen, Michael W. Keith, Robert F. Kirsch, and Dustin J. Tyler. "Intraoperative testing of selectivity of spiral nerve cuff electrodes." In Neural Engineering, 2005. Conference Proceedings, 2nd International IEEE EMBS Conference on, pp. 486-489. IEEE, 2005.

Polasek, Katharine H., Harry A. Hoyen, Michael W. Keith, Robert F. Kirsch, and Dustin J. Tyler, "Spiral Nerve Cuff Electrodes for an Upper Extremity Neuroprosthesis." In Engineering in Medicine and Biology Society, 2006. EMBS'06. 28th Annual International Conference of the IEEE, pp. 3584-3587. IEEE, 2006.

Polasek, Katharine H., Harry A. Hoyen, Michael W. Keith, and Dustin J. Typer, "Human nerve stimulation thresholds and selectivity using a multi-contact nerve cuff electrode." Neural Systems and Rehabilitation Engineering, IEEE Transactions on 15, No. 1 (2007): 76-82.

Polasek, Katherine H., Harry A. Hoyen, Michael W. Ketih, Robert F. Kirsch, and Dustin J. Tyler, "Stimulation stability and selectivity of chronically implanted multicontact nerve cuff electrodes in the human upper extremity." Neural Systems and Rehabilitation Engineering, IEEE Transactions on 17, No. 5, 428-437, 2009.

Puligopu AK, Purohit AK, Outcome of selective motor fasciculotomy in the treatment of upper limb spasticity. J Pediatr Neurosci., 6(Suppl 1):S118-25, 2011.

Rajguru SM, C. P. Richter, A. I. Matic, G. R. Holsteim, S. M. Highstein, G. M. Dittami, and R. D. Rabbitt, "Infrared photostimulation of the crista ampullaris." J Physiol 589, 1263-1294 (2011).

Rattay F and M. Aberham, "Modeling axon membranes for functional electrical stimulation," IEEE Trans Biomed Eng 40, 1201-1209 (1993).

Richter CP, Matic AI, Wells J. Jansen ED, Walsh JT—Neural stimulation with optical radiation—Laser Photonic Rev 5(1): 68-80 / DOI 10.1002/lpor.200900044 (2011).

Scguefer MA, Freeberg M, Pinault GJ, Anderson J, Hoyen H, Typer DJ, Triolo RJ. Selective activation of the human tibial and common peroneal nerves with a flat interface nerve electrode. J Neural Eng, Oct. 2013:10(5):056006, doi 10.1088/1741-2560/10/5/056006. Epub Aug. 5, 2013.

(56) References Cited

OTHER PUBLICATIONS

Schulte-Baukloh H, Bigalke H. Miller K, Heine G, Pape D, Lehmann J. Knispel HH. Botulinum neurotoxin type A in urology, antibodies as a cause of therapy failure. Int J Urol. 15(5):407-15, 2008.
Shapiro MG, Homma K, Villarreal S, Richter CP, Bezanilla F. (2012) Infrared light excited cells by changing their electrical capacitance. Nature Communications 3:736.
Sheean G. Botulinum toxin treatment of adult spasticity : a benefit-risk assessment, Drug Saf., 29(1):31-48, 2006.
Silbereis, John C., Eric J. Huang, Stephen A. Back, and David H. Rowitch. "Towards improved animal models of neonatal white matter injury associated with cerebral palsy." Disease models & mechanisms 3, No. 11-12 (2010) 678-688.
Smyth MD, Peacock WJ (2000) The surgical treatment of spasticity. Muscle Nerve. 23(2):153-63.
Verdam, Froukje J., Ruben Schouten, Jan Willem Greve, Ger H. Koek, and Nicole D. Bouvy. "An update on less invasive and endoscopic techniques mimicking the effect of bariatric surgery," Journal of obesity 2012 (2012).
Vrabec T, Bhadra N, Bhadra N, Wainright J. Kilgore KL. Non-damaging nerve conduction block using direct current. International Functional Electrical Stimulation Society Conference, Canada, 2012.
Warman, E. N. and Chiel, H.J. 1995, A new technique for chronic single extracellular recording in freely behaving animals using pipette electrodes. J. Neurosci. Methods, 57:161-169.
Wells JD, Kao C. Mariappan K, Albea J, Jansen ED, Konrad P, Mahadevan-Jansen A—Optical stimulation of neural tissue in vivo—Optics Letters 30(5): 504-6 (2005).
Wells JD, Kao C. Jansen ED, Konrad PE, Mahadevan-Jansen A—Application of Infrared Light for in vivo Neural Stimulation—J Biomed Optics 10(6): 64003-11 (2005).
Wells JD, Mahadevan-Jansen A, Bendett M. Webb J, Ralph H. Kao C. Konrad P. Jansen ED—Lasers stimulate new techniques in nerve studies—Biophotonics, (Oct. 2006).

Corning ClearCurve Optical Fiber Specification Sheets printed from http://www.corning.com/opticalfiber/products/clearcurve/single_mode_fiber.aspx, accessed Apr. 11, 2017.
Wells JD, Konrad PE, Kao CC, Jansen ED, Mahadevan-Jansen A—Pulsed laser versus electrical energy for peripheral nerve stimulation—J Neurosci Methods 163: 326-37 (2007).
Wells JD, Thomsen SL, Whittaker P. Jansen ED, Kao CC, Konrad PE, Mahadevan-Jansen A—Histological analysis reveals safety thresholds for optical nerve stimulation—Lasers Surg Med 39(6): 513-26 (2007).
Wells JD, Kao CC, Konrad PE, Milner T. Kim J. Mahadevan-Jansen A. Jansen ED—Biophysical mechanism responsible for low-level, transient optical stimulation of peripheral nerve—Biophysical J 93.2567-80 (2007).
Williamson RP. Andrews BJ. Localized electrical nerve blocking. IEEE Trans Biomed Eng, 52:362-370, 2005.
Woo MY, Campbell B. Asynchronous Firing and Block of Peripheral Nerve Conduction by 20 kC Alternating Current Bull Los Angel Neuro Soc 1964: 29:87.
Yablon SA, Brashear A, Gordon MF, Elovic EP, Turkel CC, Daggett S, Liu J, Brin MF, Formation of neutralizing antibodies in patients receiving botulinum toxin type A for treatment of postroke spasticity: a pooled-data analysis of three clinical trials. Clin Ther 29(4):683-90, 2007.
Chernov MM, Duke AR, Cayce JM, Crowder SW, Sung HJ, Jansen ED—Material considerations for optical interfacing to the nervous system—MRS Bulletin 37(6):599-605 (2012) DOI: 10.1557/mrs.2012.12.
Delgado MR, Hirtz D, Aisen M, Ashwal S, Fehlings DL, McLaughlin J, Morrison LA, Shrader MW, Tilton A, Vargus-Adams J, Practive parameter pharmacologic treatment of spasticity in children and adolescents with cerebral palsy (an evidence-based review), Neurology 74:336-343, 2010.

* cited by examiner

SYSTEMS AND METHODS FOR FAST AND REVERSIBLE NERVE BLOCK

RELATED APPLICATIONS

This application claims the benefit of U.S. Provisional Application No. 61/954,915, filed Mar. 18, 2014, entitled "SYSTEM AND METHOD FOR NERVE CONDUCTION BLOCK." This provisional application is hereby incorporated by reference in its entirety for all purposes.

GOVERNMENT SUPPORT

This invention was made with government support under DMS-101043 awarded by the National Science Foundation, R21-HL-115373, R01-NS-074149, and R01-NS-052407 awarded by the National Institutes of Health, and W811XWH-10-C-0208 awarded by the Department of Defense. The government has certain rights in the invention.

TECHNICAL FIELD

The present disclosure relates generally to systems and methods for fast and reversible nerve block and, more specifically, to systems and methods that can apply a heat signal and an electric signal to the nerve to achieve the fast and reversible block.

BACKGROUND

Patients affected with a neurological disorder are prone to chronic pain or spasmodic muscle contractions. Such chronic pain and spasticity can worsen over time without treatment. Drugs or surgery can block undesirable neural activity; however, drugs have a slow time course and may have undesirable side effects and surgery is usually irreversible. An ideal block would be fast and reversible over extended periods.

Kilohertz high-frequency alternating current (KHFAC) provides a promising new technology that reversibly blocks action potentials while still preserving nerve viability. However, nerve block associated with KHFAC is associated with an onset response, during which the nerve fires rapidly for milliseconds to seconds. The onset response can cause brief, but intense, muscle contractions and pain. To improve the clinical utility of KHFAC, the onset response should be eliminated. Increasing neural temperature can induce block (e.g., due to altered ion channel kinetics) quickly and reversibly.

SUMMARY

The present disclosure relates generally to systems and methods for fast and reversible nerve block and, more specifically, to systems and methods that can apply a heat signal and an electric signal (e.g., a kilohertz high frequency alternating current (KHFAC) signal and/or a direct current (DC) signal) to the nerve to achieve the fast and reversible block.

In one aspect, the present disclosure includes a method for blocking conduction in a nerve quickly and reversibly. A nerve block that induces heating can be applied to block conduction in the nerve. Additionally, an electrical nerve block can also be applied to block the conduction in the nerve.

In another aspect, the present disclosure includes a system that can block nerve conduction quickly and reversibly. The system includes a first nerve block modality that provides heat to the nerve to block the nerve conduction. The system also includes a second nerve block modality that provides an electrical signal to the nerve to block the nerve conduction.

In a further aspect, the present disclosure includes a neuroprosthetic system that can perform a fast and reversible nerve block. The neuroprosthetic system can include an optrode that provides heat to a nerve causing the spasticity to block conduction in the nerve. The neuroprosthetic system can also include an electrode that provides an electrical signal to the nerve to block the conduction in the nerve.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "nerve block", "nerve conduction block", and "block" can be used interchangeably when referring to the failure of impulse transmission at some point along a nerve.

As used herein, the terms "substantially blocked" and "substantial block" can interchangeably refer to a complete (e.g., 100%) or partial inhibition (e.g., less than 100%, such as about 90%, about 80%, about 70%, about 60%, or less than about 50%) of nerve conduction through a nerve. When referring to nerve block herein, it will be understood that nerve block can refer to a substantial nerve block.

As used herein, the term "nerve block modality" can refer to a particular mode in which a nerve conduction block can be applied to a nerve of a subject.

One example of a nerve block modality can include heat. The heat can be transmitted to the nerve by a signal that generates heat (a "heat signal") via one or more "optrodes". Such a signal can include an infrared (IR) light signal, a radio frequency (RF) signal, an ultrasound (US) signal, an electrical heating signal, or the like.

Another example of a nerve block modality can include electricity. The electricity can be transmitted to the nerve by an electrical signal via one or more electrodes. Such an electrical signal can include a direct current (DC) signal, an alternating current signal (AC), a high frequency alternating current signal (HFAC), a kilohertz frequency alternating current (KHFAC) signal, or the like.

As used herein, the term "nerve" can refer to one or more fibers that employ electrical and chemical signals to transmit motor, sensory and/or autonomic information from one body part to another. A nerve can refer to either a component of the central nervous system or the peripheral nervous system.

As used herein, the term "neural prosthesis" can refer to one or more devices that can be used to block nerve conduction.

As used herein, the term "onset response" can refer to a finite (e.g., several milliseconds to several seconds) burst of neuronal firing when an electrical signal (e.g., a KHFAC signal for nerve block) is first applied to a nerve.

As used herein, the terms "fast" and "quick" can be used interchangeably when referring to a nerve block that is achieved substantially instantaneously (e.g., in "real-time"). In some instances, the nerve block can be achieved within 1 second. In other instances, the nerve block can be achieved within 500 milliseconds. In still other instances, the nerve block can be achieved within 300 milliseconds. In other instances, the nerve block can be achieved within 100 milliseconds.

As used herein, the term "extended time period" can refer to a time greater than 30 minutes.

As used herein, the term "reversible" can be used to refer to a nerve block that can be applied to substantially block conduction in a nerve and then removed to substantially allow conduction in the nerve. In some instances, the nerve block can be reversed in less than 1 second. In other instances, the nerve block can be reversed in less than 500 ms. In further instances, the nerve block can be reversed in less than 200 ms. In still further instances, the nerve block can be reversed in less than 100 ms.

As used herein, the term "neurological disorder" can refer to a condition or disease characterized at least in part by abnormal conduction in one or more nerves. In some instances, the abnormal conduction can be associated with pain and/or spasticity. Examples of neurological disorders can include stroke, brain injury, spinal cord injury (SCI), cerebral palsy (CP), multiple sclerosis (MS), etc.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to systems and methods for fast and reversible nerve block and, more specifically, to systems and methods that can apply a heat signal and an electric signal (e.g., a kilohertz high frequency alternating current (KHFAC) signal and/or a direct current (DC) signal) to the nerve to achieve the fast and reversible block. The block can be delivered repeatedly without damaging neural structures, without altering the conduction properties of the nerve, and without producing systemic side effects.

In some instances, the heat signal can provide the initial block during which the electrical signal can cause spurious conduction due to an onset response. After the onset response (e.g., less than 10 seconds), the heat signal can be turned off and the electrical signal can maintain the block (e.g., for more than 30 minutes). Advantageously, by using the heat signal and the electrical signal, a nearly instant block can be achieved (e.g., within a few milliseconds) without the onset response and maintained for an extended period of time (e.g., more than 30 minutes) without damaging the nerve.

III. Systems

Figure 1:
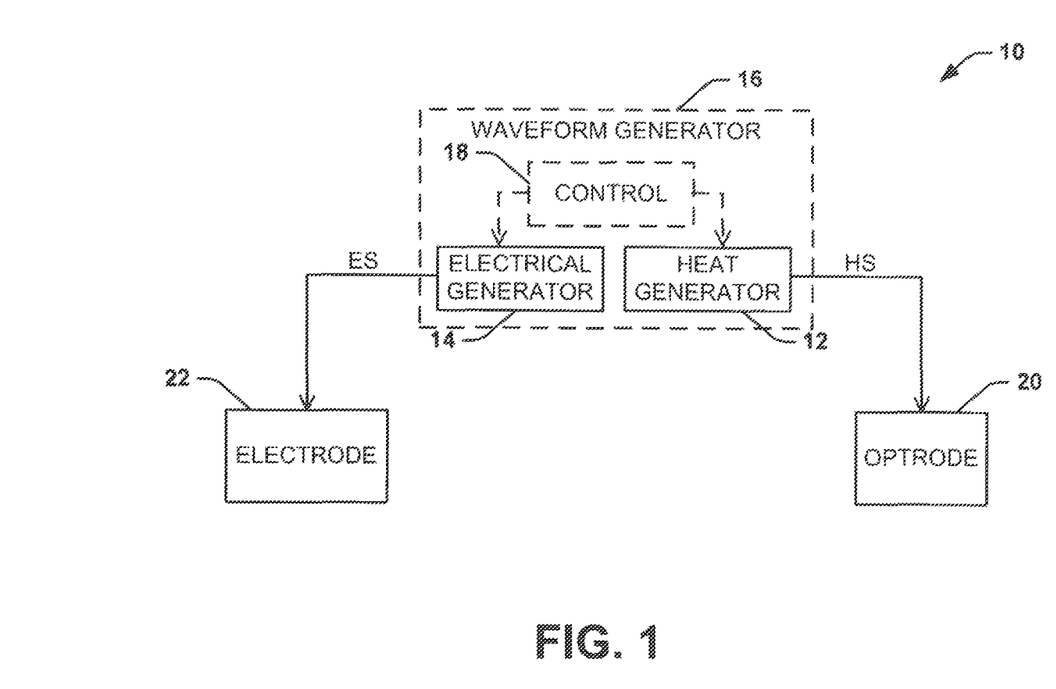
FIG. 1 is a block diagram showing a system for fast and reversible nerve conduction block in accordance with an aspect of the present disclosure.

One aspect of the present disclosure, as shown in FIG. 1, includes a system 10 that can provide fast and reversible nerve conduction block. The block can be provided by applying a heat signal (HS) to the nerve by one or more optrodes 20 and an electrical signal (ES) to the nerve by one or more electrodes. By applying the heat signal (HS) and the electrical signal (ES) in combination, the block can be achieved with lower and safer parameters for one or both of the heat signal and/or the electrical signal than either block applied alone. While not wishing to be bound by theory, it is believed that interactions between the heat block and the electrical block can allow the lower and safer block parameters by modulating nerve physiology (e.g., ion channel function). Applying the heat signal (HS) alone for an extended period of time can cause damage to the physiology of the cell so that it cannot be applied repeatedly for an extended period of time without damage. However, it can be applied repeatedly for the quick block of the onset response of the electrical signal (ES). The electrical signal (ES) can provide the maintained block, but suffers from the onset response. Additionally, the electrical signal (ES) can provide an onset response, which can be blocked by the heat signal (HS). Accordingly, the system 10 can provide a fast block, without suffering from the onset response, that provides the block for an extended period of time without damaging the nerve. For example, the block can be achieved in real time (e.g., less than 100 ms). The electrical signal (ES) can provide the prolonged block (e.g., for at least 30 minutes) that is reversible.

In some instances, the system 10 can be employed as part of a neuroprosthetic system (e.g., as part of a conduction block component) to block conduction in a nerve (e.g., to control spasticity in a muscle and/or chronic pain). For example, neuroprosthetic system can provide a user controlled spastic muscle block that can be turned off and on in real time to provide instantaneous control of spasticity.

The system 10 is illustrated schematically as a block diagram with different blocks representing different components. In some instances, the components can include a heat generator 12 operatively coupled to an optrode 20 and an electrical generator 14 operatively coupled to an electrode 22.

The heat generator 12 can generate a heat signal (HS) that can be sent to the optrode 20 for application to a nerve. The optrode 20 can include one or more devices that can deliver the heat signal (HS) to the nerve. The heat signal (HS) can provide the fast block of the conduction in the nerve. For example, upon application of the heat signal (HS), the conduction in the nerve can be blocked within one second or less. In another example, upon application of the heat signal (HS), the conduction in the nerve can be blocked within 500 ms or less. In a further example, upon application of the heat signal (HS), the conduction in the nerve can be blocked within 200 ms or less. In yet another example, upon application of the heat signal (HS), the conduction in the nerve can be blocked within 100 ms or less. Additionally, application of the heat signal (HS) does not result in the spurious nerve activity of an onset response (e.g., caused by the electrical signal (ES)).

In some instances, the heat signal (HS) can include an infrared (IR) light signal, a light signal, a radio frequency (RF) signal, an ultrasound (US) signal, and/or an electrical heating signal. The optrode 20 can include one or more devices that can be used to apply the heat signal (HS) to the nerve. As an example, the optrode 20 can include one or more IR lasers when the heat signal (HS) is an IR light signal. In another example, the optrode can include one or more heating devices when the heat signal (HS) is an electrical heating signal. In a further example, the optrode can include one or more fiber optic devices when the heat signal (HS) is a light signal.

The electrical generator 14 can generate an electrical signal (ES) that can be sent to the electrode 22 for application to the nerve. The electrode 22 can include one or more devices, elements, or components that can apply the electrical signal (ES) to the nerve. In some instances, the electrical signal (ES) can include a direct current (DC) signal, an alternating current (AC) signal, a high frequency alternating current (HFAC) signal, and/or a kilohertz frequency alternating current (KHFAC) signal. The electrical signal (ES) can provide the block for an extended time period. For example, upon application of the electrical signal (ES), the conduction of the nerve can be blocked for 30 minutes or more. The block can be maintained without damaging the neural response, allowing the block to be reversed to enable conduction in the nerve (e.g., within one second or less). However, application of the electrical signal (ES) can evoke an onset response. Accordingly, the heat signal (HS) can be applied to block the evoked onset response.

Figure 2:
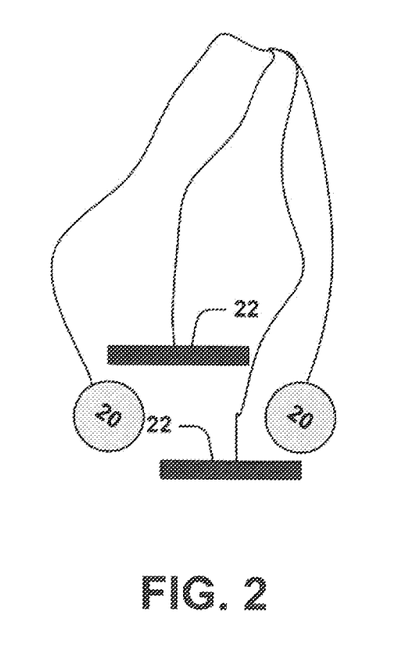
FIGS. 2 and 3 are schematic illustrations showing exemplary configurations of the system in FIG. 1.
Figure 3:
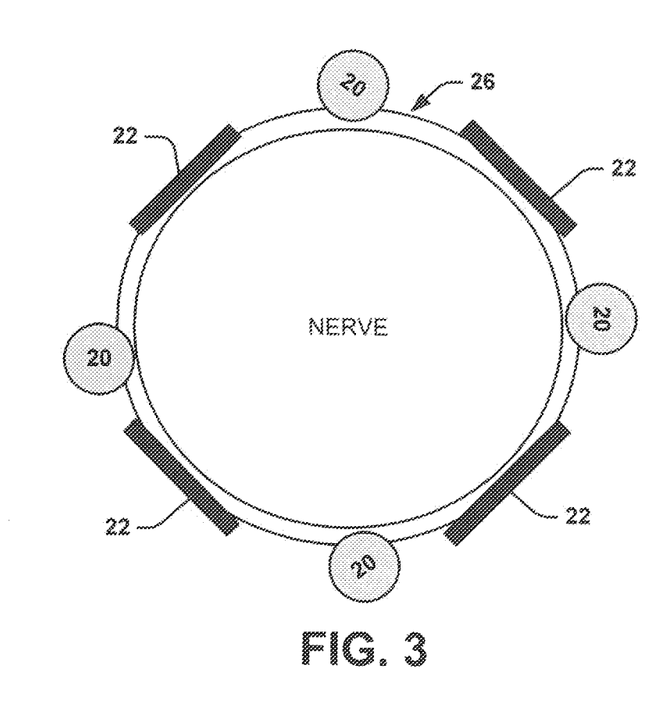

The optrode 20 and the electrode 22 can apply the heat signal (HS) and the electrical signal (ES), respectively, to the nerve. In some instances, as shown in FIG. 2, a plurality of optrodes 20 and a plurality of electrodes 22 can be separate devices, each arranged near the nerve. In other instances, as shown in FIG. 3, the plurality of optrodes 20 and the plurality of electrodes 22 can be combined within a single device, such as a nerve cuff electrode 26. Although two optrodes and two electrodes are illustrated in FIG. 2, and four optrodes and four electrodes are illustrated in FIG. 3, it will be understood that the number of optrodes and electrodes need not be equal, and could be greater or fewer than that illustrated.

Referring again to FIG. 1, in some instances, the heat generator 12 and the electrical generator 14 can be included as part of a waveform generator 16. The waveform generator 16 can include a control device 18 that can regulate the timing, the strength (e.g., amplitude, frequency, etc.), and/or other parameters of the application of the heat signal (HS) and the electrical signal (ES). In some instances, the functions of the control device 18 can be implemented by computer program instructions. These computer program instructions can be stored in a non-transitory memory and provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the control 18 device specified in the block diagrams.

Figure 4:
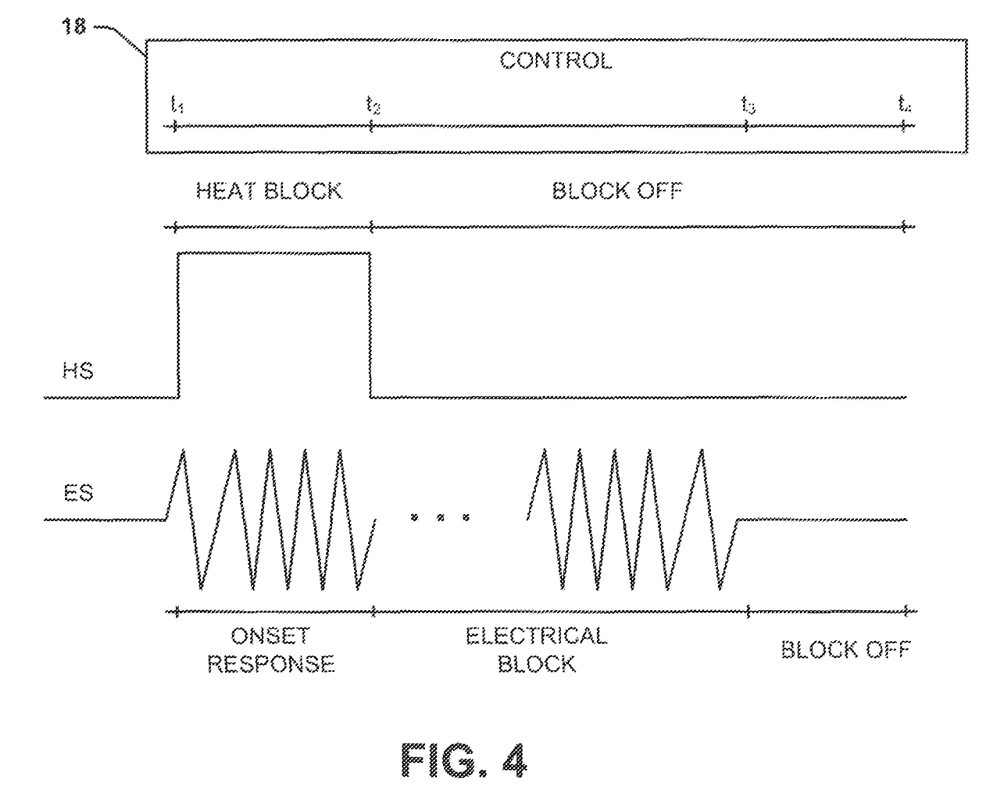
FIGS. 4-6 are schematic depictions of a heat signal and an electrical signal that can be used by the system in FIG. 1 to block nerve conduction.
Figure 5:
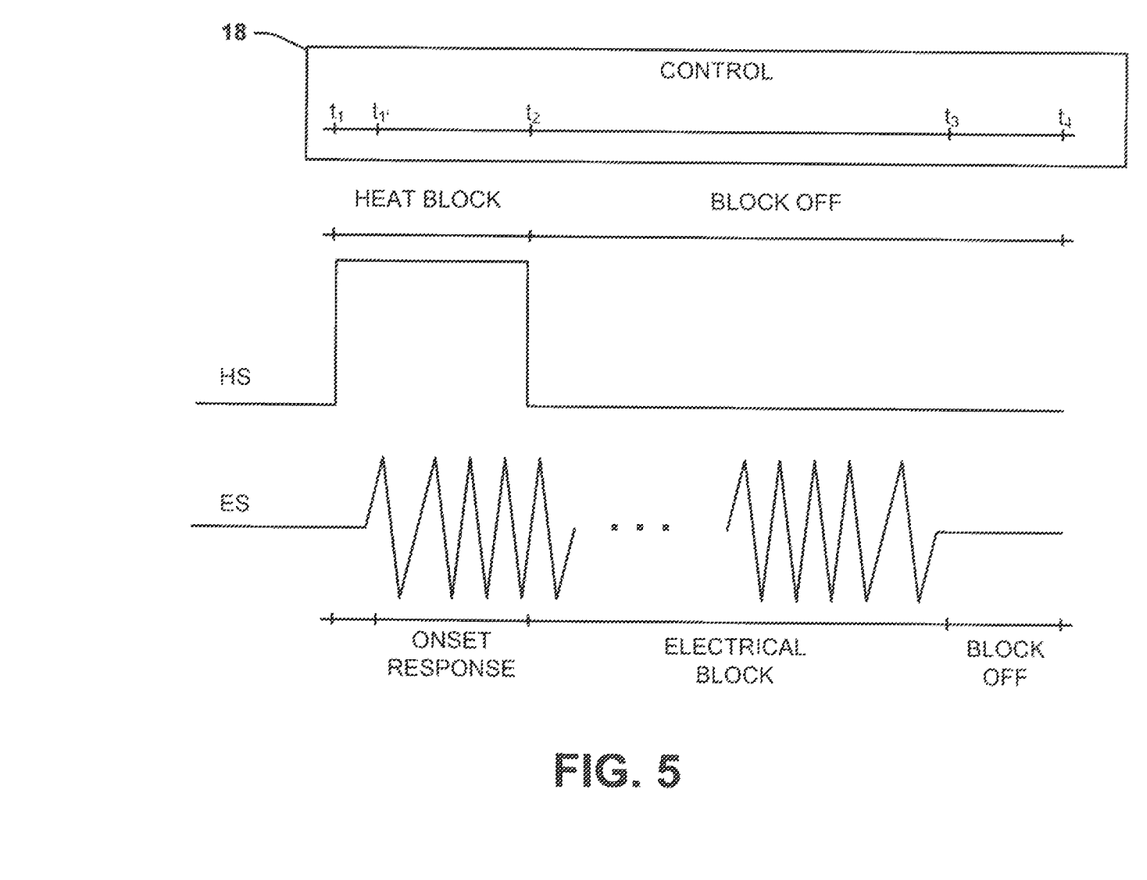
Figure 6:
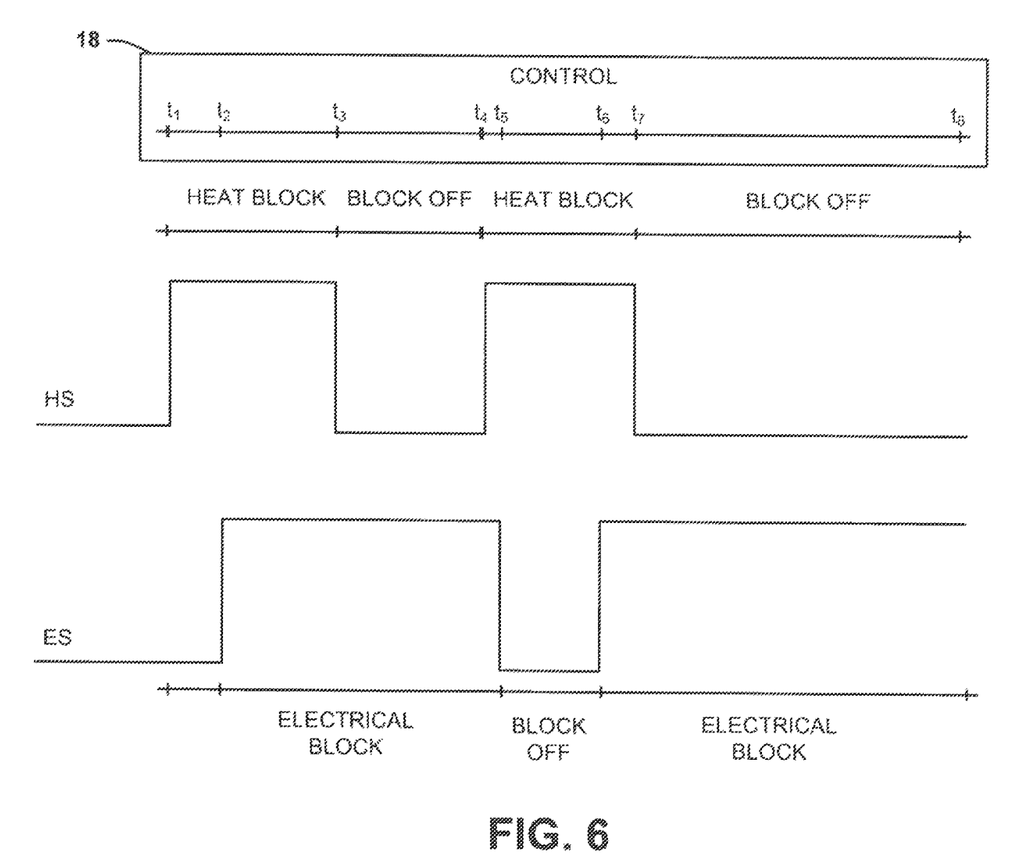

Different examples of timing patterns or functions that can be employed by the control device 18 are shown in FIGS. 4-6. In each case, the heat signal (HS) and the electrical signal (ES) can provide an instant block without the onset response, an extended block without damaging the nerve, a quickly reversible block, and a block that can be delivered repeatedly without damaging neural structures, without altering the conduction properties of the nerve, and without producing systemic side effects. The heat signal (HS) can be applied at least during an onset response generated by the electrical (ES) to block the onset response. For example, the heat signal (HS) can be applied from 1-10 seconds until the onset response resolves. This allows the heat signal (HS) to provide the block without the risk of thermally induced tissue damage. The electrical signal (ES) can provide the block after resolution of the onset response for an extended time period (e.g., at least 30 minutes). Upon removing the block, it is quickly reversible (e.g., allowing conduction in less than 1 second).

In FIG. 4, the heat signal (HS) and the electrical signal (ES) can be applied simultaneously (e.g., both are applied at $t_1$). The electrical signal (ES) can be a KHFAC signal that can provide an onset response that is blocked by the heat signal (HS). The heat signal (HS) can be stopped when the onset response resolves (e.g., at $t_2$). The electrical signal (ES) can provide a block over an extended period of time (e.g., at least 30 minutes). When the electrical signal (ES) is turned off (e.g., at $t_3$), normal function can return to the nerve instantly or almost instantly (e.g., within 1 second). FIG. 5 is similar to FIG. 4, except the electrical signal (ES) is applied slightly after the heat signal (ES) is applied (e.g., at $t_1$). The delay of the electrical signal (ES) with respect to the heat signal (HS) can ensure that the heat signal (HS) has already established the block before the onset response so that the heat signal (HS) is assured of blocking the onset response. FIG. 6 depicts alternating the heat signal (HS) and the electrical signal (ES). As illustrated, the electrical signal (ES) can be a DC signal. As illustrated, the heat signal (HS) and the electrical signal (ES) can overlap in time. Even thought, as illustrated, the amplitudes of the signals remains constant, in some instances, the amplitude of the signals can be sequentially modulated.

IV. Methods

Figure 7:
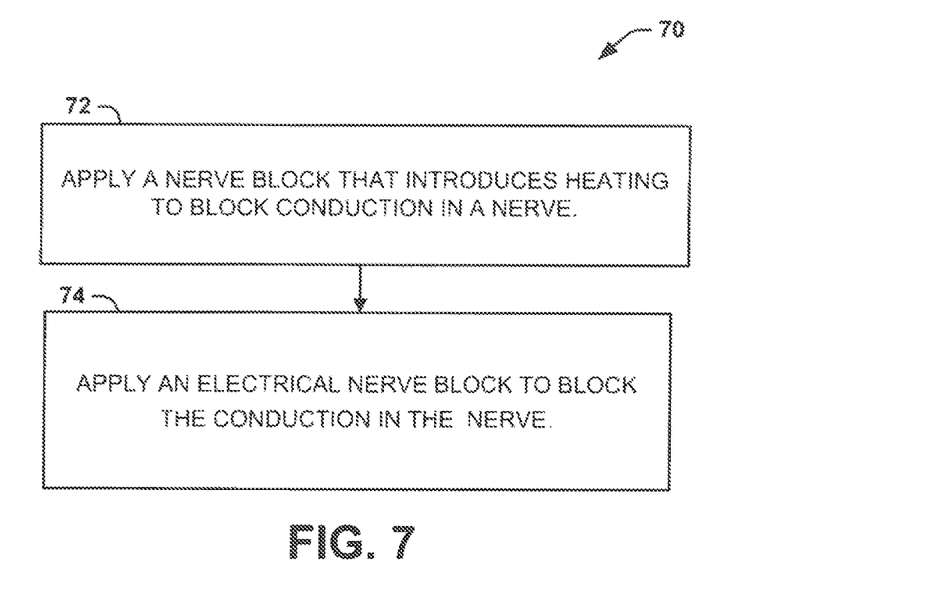
FIG. 7 is a process flow diagram illustrating a method for fast and reversible nerve conduction block according to another aspect of the present disclosure.
Figure 8:
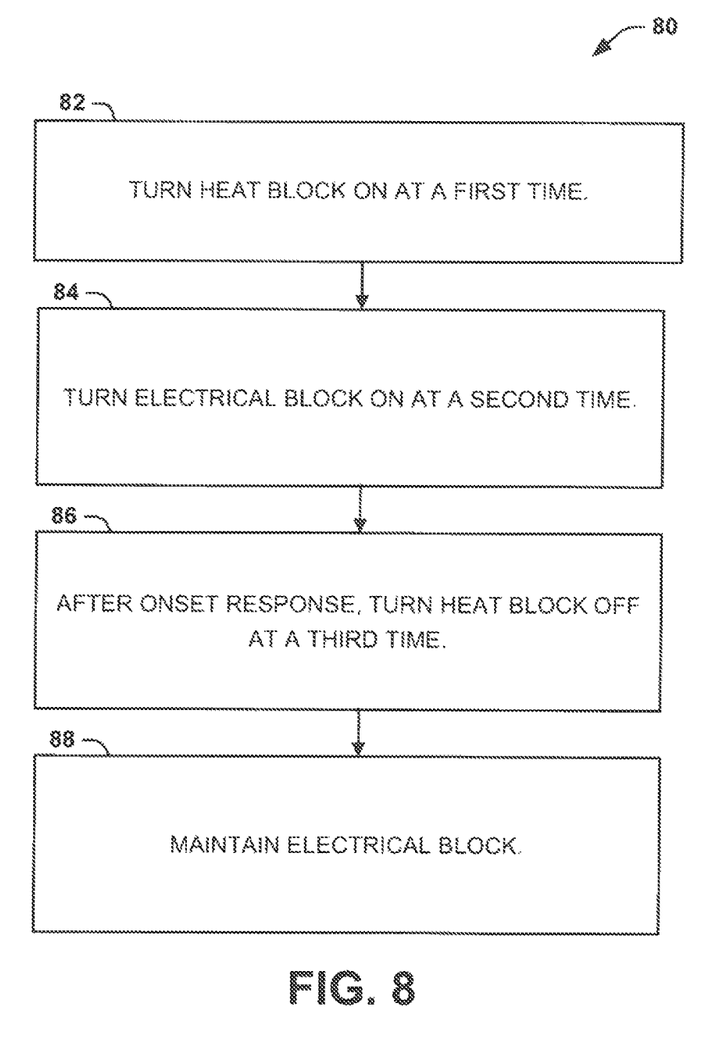
FIG. 8 is a process flow diagram illustrating a method for controlling the nerve conduction block in FIG. 7.

Another aspect of the present disclosure includes methods that can provide fast and reversible nerve conduction block. An example of a method 70 that can block the conduction in the nerve is shown in FIG. 7. Another example of a method 80 for controlling the nerve conduction block in FIG. 7 is shown in FIG. 8. The methods 70 and 80 are illustrated as process flow diagrams with flowchart illustrations. For purposes of simplicity, the methods 70 and 80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

As shown in FIG. 7, the method 70 can provide fast and reversible nerve conduction block. The method 70 can apply a heat signal and an electrical signal to the nerve to achieve such a block. Indeed, the block can be applied for an extended period of time (e.g., 30 minutes or more) without damaging the nerve, quickly reversible (e.g., within 1 second), and delivered repeatedly without damaging neural structures, without altering the conduction properties of the nerve, and without producing systemic side effects.

At 72, a nerve block that introduces heating (e.g., via a heating signal (HS)) can be applied to a nerve (e.g., via optrode 20) to block conduction in the nerve. At 74, an electrical nerve block (e.g., via an electrical signal (ES)) can be applied to the nerve (e.g., via electrode 22) to block the conduction in the nerve. In some instances, the nerve block that induces heating (e.g., via the heating signal (HS)) can be applied at least during an onset response generated by the electrical nerve block (e.g., via the electrical (ES)) to block the onset response. The electrical nerve block (e.g., via the electrical signal (ES)) can be maintained over an extended time period. The nerve block can be achieved quickly (e.g., within 1 second) and quickly reversible (e.g., within 1 second).

One example of a method 80 for controlling the nerve conduction block in FIG. 7 (e.g., by control 18 device of FIG. 1) is shown in FIG. 8. This example is shown to control the onset response of the electrical signal. In some instances, one or more of the steps of method 80 can be stored in a non-transitory memory device and executed by a processor.

At 82, the heat block can be turned on at a first time. At 84, the electrical block can be turned on at a second time. In one example, the first time and the second time can be equivalent (e.g., as shown in FIG. 4) so that the blocks are applied simultaneously. In another example, the first time and the second time can be different (e.g., as shown in FIG. 5), but the blocks are thereafter applied simultaneously. At 86, after the onset response of the electrical block, the heat block can be tired off at a third time. For example, the nerve block that induces heating can be applied from 1-10 seconds until the onset response resolves. This allows the heat block to provide the block without the risk of thermally induced tissue damage. At 88, the electrical block can be maintained while the heat block is turned off. The electrical block can provide the block after resolution of the onset response for an extended time period (e.g., at least 30 minutes). Upon removing the block, it is quickly reversible (e.g., allowing conduction in less than 1 second).

V. Example

The following example is for the purpose of illustration only and is not intended to limit the scope of the appended claims.

Example

This example demonstrates a fast and reversible nerve block without an onset response using a KHFAC electrical nerve block and an optical nerve block using IR lasers [alternating current and infrared (ACIR)].

Methods
Animal Preparation

Unmyelinated nerves of *Aplysia* were used. *Aplysia* can be maintained for many hours and have previously been used to define appropriate parameters for optical block in myelinated rat sciatic nerve. Animals 300 to 400 g were used, as their nerves are 4 to 7 cm, with a diameter of 0.5 to 1.5 mm, comparable to rat sciatic nerve. Animals were anesthetized with isotonic magnesium chloride. The pleural-abdominal nerves were maintained in *Aplysia* saline at room temperature after dissection. All experiments were performed in vitro.

Experimental Setup

Figure 9:
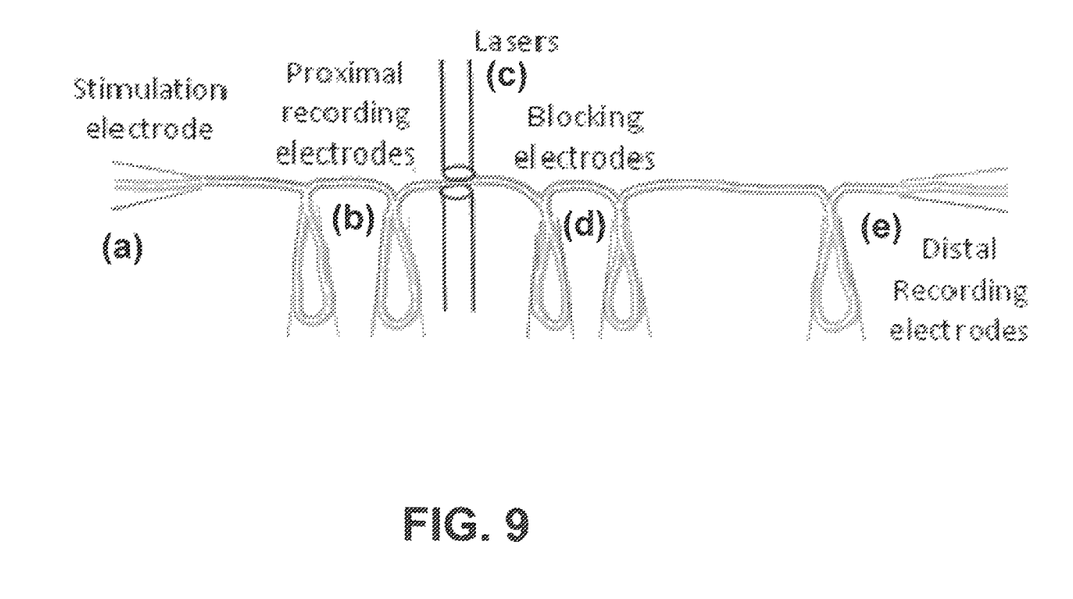
FIG. 9 is a schematic illustration of a nerve preparation incorporating kilohertz high frequency alternating current (KHFAC) and infrared (IR) lasers.

Suction electrodes were placed on the nerve as shown schematically in FIG. 9. A monopolar suction electrode delivered stimulus pulses (a); a pair of en passant electrodes constituted a bipolar proximal recording electrode (b). Two lasers were placed across the nerve (c); a bipolar en passant electrode delivered the KHFAC block (d). A pair of electrodes served as a bipolar distal recording electrode (e). En passant electrodes were chosen for convenience; preliminary data demonstrated that the cuff electrodes could also be used. Each electrode was filled with *Aplysia* saline solution before suctioning the nerve into the electrode to preserve nerve viability. An Ag/AgCl wire was inserted in each electrode. Electrical stimulation to generate nerve action potentials was controlled by a pulse generator unit (A310 Accupulser, WPI Instruments) via a stimulus isolator (WPI A360, WPI Instruments). KHFAC block was delivered by a controlled constant-current function generator (Keithley 6221) using a sinusoidal waveform. An inductor (8.2 H) was placed across the function generator outputs to minimize DC leakage. The nerve compound action potential (CAP) was monitored using AxoGraph X (AxoGraph Scientific).

Two Capella lasers [Lockheed Martin Aculight, centered at 1860 and 1863 nm and coupled into 600-μm multimode fibers (P600-2-VIS-NIR, Ocean Optics, Dunedin, Fla.)] were placed between the proximal recording and the KHFAC blocking electrodes (e.g., FIG. 9(c)). The small wavelength difference between the lasers was due to different wavelength tuning ranges; water absorption coefficients were similar. The two optical fibers were placed on either side of the same nerve cross section to ensure more uniform IR exposure. A typical sheath thickness is about 100 μm. Since the optical fibers gently touched the nerve sheath, spot size at the nerve surface was 600 μm. The fiber had a numerical aperture of 0.22 (i.e., a beam divergence of 25.4 deg in air), so the spot was slightly larger at the axons due to divergence and scattering. Since the onset response travels both anterogradely and retrogradely from the KHFAC block electrode, applying the lasers to block the onset response near the proximal electrode allowed the distal electrode to serve as a control for the same KHFAC block. Varying placement of the optical fibers between the KHFAC and the distal or proximal recording electrodes had no effect on the results.

Experimental Protocol

Three experiments were performed on three different nerves, using an A-B-A protocol. During protocol A, a train of action potentials was blocked by KHFAC; protocol B added IR inhibition to generate onset response block. Protocol A was repeated as a control. A current just above the stimulation threshold produced CAPs of sufficient amplitude to assess block effectiveness. The minimum amplitude KHFAC waveform at which block was observed was consistently at a frequency of 10 kHz and amplitude ranging from 10 to 15 mA (peak-to-peak). For the two lasers, radiant exposures per pulse ranged from 0.177 to 0.254 J/cm2. Both lasers were switched on at the same time and emitted laser light for 30 s before the KHFAC waveform was applied, using 200-μs pulses at 200 Hz, to allow the temperature to reach a higher value. Nerve health was assessed before and after every experiment by comparing the propagating CAPs traveling down the length of the nerve.

Results

Figure 10:
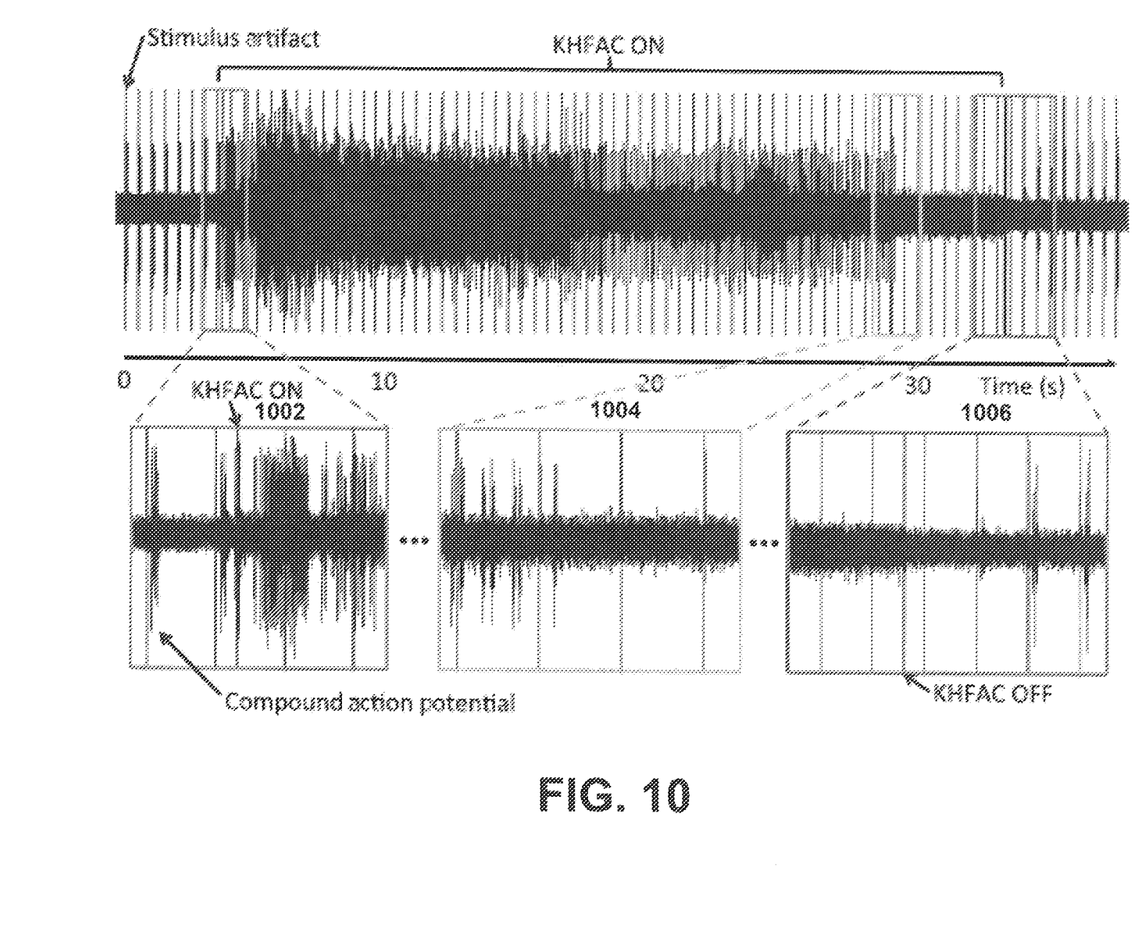
FIG. 10 is an illustration of the onset response seen with KHFAC block as recorded through the distal recording electrode.

FIG. 10 shows that application of KHFAC induced both an onset response (1002), and that it completely blocked the CAP (1004), which returns after KHFAC was turned off (1006).

Figure 11:
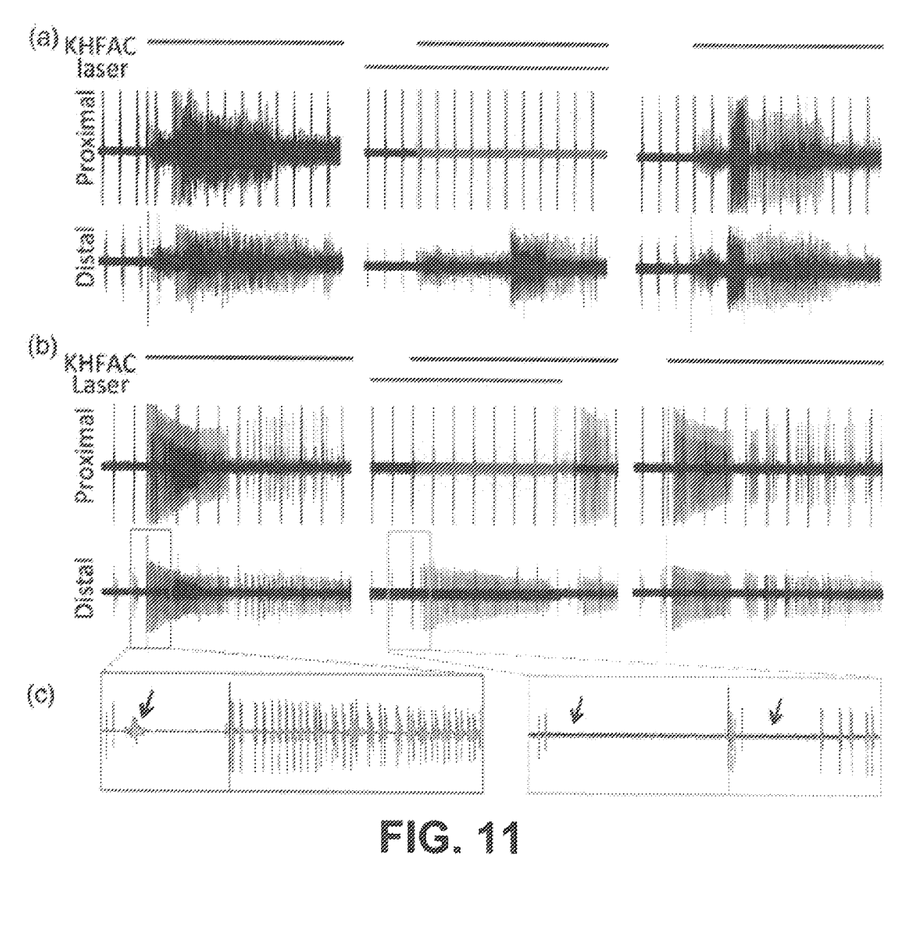
FIG. 11 is an illustration of the onset response seen with KHFAC block and IR block.

When only KHFAC is applied (FIGS. 11(a) and 11(b), left panels), the onset response is visible in both the proximal and distal recordings. When IR is also applied, the onset response is blocked in the proximal recording only (FIGS. 11(a) and 11(b), middle panels, shaded rectangles). The onset response was still present at the distal recording because the onset response's propagation to that electrode was unaffected by the laser (FIGS. 9(d) and 9(e)). Although the onset response was present in the distal recording, the CAP was blocked by the laser (FIG. 11(c)). The onset response reappeared proximally as soon as the laser was turned off (FIGS. 11(a) and 11(b), right panels). After ACIR, CAPs were triggered and had the same amplitude as before ACIR, demonstrating its reversibility. ACIR produced complete onset response block in each experiment (N ¼ 3). The onset response, which has previously been shown to be variable over time, was not identical before, during, and after block, but the block of the onset response was always complete.

From the above description, those skilled in the art will perceive improvements, changes and modifications. For example, in some instances, nerve conduction block according to the systems and methods of the present invention can be used to treat pain or spasticity. Such improvements, changes and modifications are within the skill of one in the art and are intended to be covered by the appended claims.

What is claimed is:

1. A system, comprising:
    a heat generator configured to provide a heat signal to an optrode, wherein the optrode is configured to apply the heat signal to a nerve to block conduction;
    an electrical generator configured to provide an electrical signal to an electrode, wherein the electrode is configured to apply the electrical signal to the nerve to block conduction; and
    a control device comprising a processor to regulate timing of the heat signal and the electrical signal,
    wherein the heat signal and the electrical signal are applied simultaneously for a first period of 1 second or less so that the heat signal blocks an onset response in the nerve generated by the electrical signal, and after the first period of 1 second or less, the heat signal is stopped and the electrical signal is applied alone over a second period of at least one minute after the onset response.

2. The system of claim 1, wherein the heat generator is configured to provide, through the optrode, at least one of an infrared light signal, a radio frequency signal, an ultrasound signal, and an electrical heating signal; and
    wherein the electrical generator is configured to provide, through the electrode, at least one of a DC signal and a KHFAC signal.

3. The system of claim 1, wherein the heat generator is configured to provide an infrared light signal through the optrode and the electrical generator is configured to provide a KHFAC signal through the electrode.

* * * * *

UNITED STATES PATENT AND TRADEMARK OFFICE
CERTIFICATE OF CORRECTION

| | | |
|---|---|---|
| PATENT NO. | : 10,758,738 B2 | Page 1 of 1 |
| APPLICATION NO. | : 15/126610 | |
| DATED | : September 1, 2020 | |
| INVENTOR(S) | : Chiel et al. | |

It is certified that error appears in the above-identified patent and that said Letters Patent is hereby corrected as shown below:

In the Specification

Column 1, Line 14 after the heading GOVERNMENT SUPPORT before the TECHNICAL FIELD HEADING, please replace that paragraph with the below:
--This invention was made with government support under NS074149, HL115373, and NS052407 awarded by the National Institutes of Health; W81XWH-10-C-0208 awarded by the Department of Defense; and 1010434 awarded by the National Science Foundation. The government has certain rights in the invention.--

Signed and Sealed this
Ninth Day of December, 2025

John A. Squires
*Director of the United States Patent and Trademark Office*